US012276587B2

(12) United States Patent
Durucan et al.

(10) Patent No.: US 12,276,587 B2
(45) Date of Patent: Apr. 15, 2025

(54) METHOD FOR PREPARING A SUBSTRATE BY APPLYING A SAMPLE TO BE ANALYSED

(71) Applicant: Danmarks Tekniske Universitet, Kgs. Lyngby (DK)

(72) Inventors: Onur Durucan, Dyssegaard (DK); Michael Stenbaek Schmidt, Copenhagen SV (DK); Tomas Rindzevicius, Malmoe (SE); Anja Boisen, Birkeroed (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 0 days.

(21) Appl. No.: 18/483,209

(22) Filed: Oct. 9, 2023

(65) Prior Publication Data
US 2024/0035939 A1  Feb. 1, 2024

Related U.S. Application Data

(63) Continuation of application No. 16/097,939, filed as application No. PCT/EP2017/060314 on May 1, 2017, now Pat. No. 11,815,440.

(30) Foreign Application Priority Data

May 2, 2016 (EP) ................................. 16167956

(51) Int. Cl.
*G01N 1/40* (2006.01)
*B01L 3/00* (2006.01)
(Continued)

(52) U.S. Cl.
CPC ........ *G01N 1/4077* (2013.01); *B01L 3/50273* (2013.01); *B01L 3/502753* (2013.01);
(Continued)

(58) Field of Classification Search
CPC ............... B01L 3/5027; B01L 3/50273; B01L 3/502753; B01L 2200/0684;
(Continued)

(56) References Cited

U.S. PATENT DOCUMENTS

2002/0076354 A1  6/2002  Cohen
2009/0191643 A1* 7/2009  Boehm ................. B01L 3/5023
                                                                      436/164

(Continued)

FOREIGN PATENT DOCUMENTS

EP  0211334 A1  2/1987
EP  2878373 A1  6/2015

(Continued)

OTHER PUBLICATIONS

Written Opinion of the International Searching Authority PCT/ISA/237 for International Application No. PCT/EP2017/060314 dated Jul. 4, 2017.

(Continued)

*Primary Examiner* — Matthew D Krcha
*Assistant Examiner* — Austin Q Le
(74) *Attorney, Agent, or Firm* — Harness, Dickey & Pierce, P.L.C.

(57) ABSTRACT

The invention relates to a method for preparing a substrate comprising a sample reception area and a sensing area. The method comprises the steps of: 1) applying a sample on the sample reception area; 2) rotating the substrate around a predetermined axis; 3) during rotation, at least part of the liquid travels from the sample reception area to the sensing area due to capillary forces acting between the liquid and the substrate; and 4) removing the wave of particles and liquid formed at one end of the substrate. The sensing area is closer (Continued)

to the predetermined axis than the sample reception area. The sample comprises a liquid part and particles suspended therein.

6 Claims, 6 Drawing Sheets

(51) Int. Cl.
*G01N 21/07* (2006.01)
*G01N 21/65* (2006.01)
*G01N 33/49* (2006.01)
*G01N 35/00* (2006.01)

(52) U.S. Cl.
CPC ........... *G01N 21/07* (2013.01); *G01N 21/658* (2013.01); *G01N 33/491* (2013.01); *G01N 35/00069* (2013.01); *B01L 2200/0684* (2013.01); *B01L 2300/0803* (2013.01); *B01L 2300/087* (2013.01); *B01L 2400/0406* (2013.01); *B01L 2400/0409* (2013.01); *G01N 2035/00158* (2013.01); *G01N 2035/00495* (2013.01)

(58) Field of Classification Search
CPC ....... B01L 2300/0803; B01L 2300/087; B01L 2400/0406; B01L 2400/0409; G01N 1/4077; G01N 21/07; G01N 21/658; G01N 33/491; G01N 35/00069; G01N 2035/00158; G01N 2035/00495
See application file for complete search history.

(56) References Cited

U.S. PATENT DOCUMENTS

| | | |
|---|---|---|
| 2010/0112723 A1 | 5/2010 | Battrell et al. |
| 2013/0074962 A1 | 3/2013 | Garcia da Fonseca et al. |
| 2013/0243664 A1 | 9/2013 | Boehm et al. |
| 2015/0093771 A1 | 4/2015 | Griss et al. |
| 2015/0153283 A1* | 6/2015 | Huang .............. G01N 33/54386 506/13 |
| 2016/0047794 A1 | 2/2016 | Saiki |
| 2018/0280969 A1 | 10/2018 | Moura Pires De Andrade Tenreiro et al. |

FOREIGN PATENT DOCUMENTS

| | | |
|---|---|---|
| JP | 2009014529 A | 1/2009 |
| WO | WO-0243866 A2 | 6/2002 |

OTHER PUBLICATIONS

International Search Report PCT/ISA/210 for International Application No. PCT/EP2017/060314 Dated Jul. 4, 2017.
Neus Godino, "Centrifugally enhanced paper microfluidics," MEMS 2012, Paris, France, dated Jan. 29, 2012-Feb. 2, 2012.
Carl Burtis, "Development of a simple device for processing whole blood samples into measure aliquots of plasma", Clinical Chemistry, vol. 32, No. 9, dated Sep. 1, 1986.
Neus Godino, "A centrifuge-pneumatic cascade for fully integrated and multiplexed biological analysis", MEMS 2012, Paris, France, dated Jan. 29-Feb. 2, 2012.
Hyundoo Hwang, "Paper on a disc: balancing the capillary-driven flow with a centrifugal force," Lab Chip 2011, vol. 11, 3404-3406, dated May 24, 2011-Jul. 29, 2011.

* cited by examiner

METHOD FOR PREPARING A SUBSTRATE BY APPLYING A SAMPLE TO BE ANALYSED

CROSS-REFERENCE TO RELATED APPLICATIONS

This is a continuation application of U.S. application Ser. No. 16/097,939, filed Oct. 31, 2018, which is a national phase under 35 U.S.C. § 371 of PCT International Application No. PCT/EP2017/060314 which has an International filing date of May 1, 2017, which claims priority to European Application No. 16167956.8, filed May 2, 2016, the entire contents of each of which are hereby incorporated by reference.

FIELD OF THE INVENTION

The present invention relates to a method for preparing a substrate by applying a sample to be analysed.

BACKGROUND OF THE INVENTION

The invention relates to a separation of a sample comprising a liquid part and a higher density component, such as a higher density liquid or a colloid, by rotation, a transportation of the liquid to a sensing area of a substrate by capillary forces acting against a centrifugal force created by rotation. A problem to be solved by the invention is the management of at least a portion of the sample remaining at the substrate. Similar technologies have been discussed in a number of prior art documents. These include EP 0211334 A1, "Centrifugally enhanced paper microfluidics", Neus Godino, et al., 2012 Jan. 29; "Development of a simple device for processing whole blood samples into measure aliquots of plasma", Carl Burtis, et al., 1986Sep. 1. EP 2 878 373 A1, US 2016/047794, WO 02/43866, JP 2009 014529, "A centrifuge-pneumatic cascade for fully integrated and multiplexed biological analysis", Neus Godino, et al., 2012 Jan. 29, US 2015093771 A1, WO 0243866 A2, and "Paper on a disk: balancing the capillary-driven flow with a centrifugal force." Lab on a Chip 11.20 (2011): 3404-3406 by Hwang, Hyundoo, et al. However, none of these solve a problem of the excess sample management.

EP 0211334 A1 relates to a disk which prepares a whole blood sample for further analysis. Rotating the disk, the whole blood sample is separated into serum and solids by centrifugal forces. After the separation, the disk rotation is stopped and the serum travels to the analysis chambers, due to capillary forces. However, the method requires a precisely measured sample, thus, adding a complexity to the entire method.

US 2015093771 A1 presents an analytical device for analysis of different samples, as well as a method for using the device. One of the steps of the method is rotation of the device by filling a sample dosing chamber with an appropriate amount of sample. The rotation of the device also causes mixing of a sample with a reagent in a mixing chamber. Rotation, i.e. the centrifugal force is further used for separating plasma from whole blood. Different microfluidic valves, which retain the liquid at low rotational speeds but allow it to pass at higher speeds, are used.

WO 0243866 A2 describes a disk for separating liquid and particles of a particulate suspension. The disk comprises a separation chamber and a metering chamber connected by a conduit. When the disk is rotated, particles are separated from the liquid part of the suspension by the centrifugal force. Microfluidic valves, here in the form of capillary passages, are used for retaining liquid at lower rotational speeds and allow it to pass at higher speeds.

Lab on a Chip 11.20 (2011): 3404-3406 describes an active control of the capillary driven flow in paper, where a centrifugal force counteracts capillary forces. It relates to the controlling of capillary flow oppositely to the centrifugal forces. This reference, however, does not describe the use of this method for separating a liquid from a colloid and therefore it does not describe application of a sample onto a substrate, as well as a sample management.

OBJECT OF THE INVENTION

It is an object of embodiments of the present invention to provide an efficient and simple management of at least a portion of the sample remaining at the substrate.

DESCRIPTION OF THE INVENTION

In a first aspect, the present invention relates to a method for preparing a substrate comprising a sample reception area and a sensing area, the substrate being positioned in a sensing chamber, the method comprising the steps of:
- applying a sample to the sample reception area, the sample comprising a liquid part having a first density and a sample part having a second density being higher than the first density;
- rotating, with a first rotational frequency, the substrate around a predetermined axis, the sensing area being closer to the predetermined axis than the sample reception area;
- during rotation, at least part of the liquid part travels from the sample reception area to the sensing area due to first capillary forces acting between the liquid part and the substrate; and
- decreasing the rotational frequency to a second rotational frequency and transferring at least a portion of the sample remaining at the sample reception area to a waste chamber separate from the sensing chamber.

The method may be used in the food industry, for environmental purposes, in hospitals, etc.

The sample comprises a liquid part having a first density and a sample part having a second density being higher than the first density. The sample may be any type of fluid. The sample may be a body fluid, such as blood, serum, urine, saliva, milk, etc. It may alternatively be any other type of fluid such as oil, vine, beer, juice, coffee or any other beverage. Furthermore, the sample may be any kind of dairy product such as milk, yogurt, or the like. The sample may alternatively be selected from a group of toxic fluids. In addition, the sample may be selected from solid food such as meat, vegetables, coffee beans, spices, seeds, flavours, etc., which would be dissolved in a suitable solvent in order to create a liquid.

The sample part having the second density may comprise a liquid and/or molecules or particles. Such molecules or particles may differ in size and/or weight/density. The molecules or particles may be suspended or precipitated into the liquid part of the sample. For example, when the sample is whole blood, blood plasma may represent the liquid part of the sample part having the first density where the sample part having the second density may comprise e.g. blood cells.

The sample may comprise a solvent. A number of reasons exist for adding a solvent. For example, a solvent may be added in cases when the substrate has low or non-wetting properties for the sample. The solvent then could serve to increase the wetting properties of the substrate for the sample and to increase the strength of the capillary forces between the liquid part and the substrate and therefore a good matching between the sample and substrate. Solvents may also be added in order to dissolve molecules or particles in an original sample in order to form the liquid part. Typically, solvents such as acetone, ethanol, isopropanol, methanol, etc. may be used.

The sample to be analysed may be applied onto the substrate manually, or the process can be automated, such as by use of a microfluidic platform.

The substrate comprises a sample reception area and a sensing area. The sample reception area serves for receiving the sample, i.e. the sample is applied to the sample reception area. This area preferably occupies a first portion of the substrate. The sample sensing area then may occupy a second portion of the substrate. The sample sensing area may be non-overlapping with the sample reception area, or these two areas may be partially overlapped. Typically, the sample sensing area is a continuation of the sample reception area, such as two portions of the same element and/or the same surface. The sample sensing area may comprise features which enable sensing and detection of chemical properties of the liquid part. The sample reception area may get in touch with the sample before the sample sensing area.

During the rotating step, a separation of the sample may take place, as the rotation creates a centrifugal force directed away from the axis. The predetermined axis of rotation may be selected in any desired manner. Typically, the substrate may be rotatable around an axis which is perpendicular to a main surface of the substrate. However, other axes of rotation may be selected. The sensing area of the substrate is closer to the predetermined axis than the sample reception area, so that the sample part having the second density is prone to positioning itself farther away from the sensing area than the liquid part.

Preferably, the sample is applied to the sample reception area before or during the substrate rotation with a first rotational frequency. Providing the sample to the sample reception area, while a rotation takes place, has the advantage that the sample is forced away from the sensing area so that an initial pollution of the sensing area with the sample part having the second density may be avoided. Naturally, this initial rotation may be used also for providing the sample to the sample reception area and may have any rotational frequency, which may very well be different from the first and second rotational frequencies.

During the rotation step, at least a part of the liquid part travels from the sample reception area to the sensing area by first capillary forces. Thus, the substrate may comprise a portion configured to bring about such capillary forces, such as one or more channels, pillars, paper, a braid, a woven, non-woven and/or knitted element. Furthermore, any kind of structure having nano- and/or micro-scale structures resulting in rough surface structures, such as porous, mesh-like, cone-like, rectangular, etc., may be used.

After the rotation step, the rotational frequency is decreased from the first rotational frequency to a second, lower rotational frequency. This reduces the centrifugal forces acting on the sample. During the reducing step, a portion of the sample may remain at the sample reception area of the substrate. If this portion is not removed, it may wash over the sensing area of the substrate once the rotation is reduced or completely stopped. This portion of the sample remaining at the sample reception area of the substrate is removed when the rotational frequency is reduced.

Once the at least part of the liquid part of the sample reaches the sensing area of the substrate, any type of measurement and analysis of the sample can be performed. An analysis step may be performed during or after the decreasing step.

The first rotational frequency may be selected so that the first centrifugal force acting on the part of the sample having the second density is larger than the capillary forces created by the substrate on this second density part. Additionally or alternatively, the part of the sample having the second density may be formed by e.g. particles which may be physically restrained by the substrate from reaching the sensing area.

Capillary forces are often related with to intermolecular interaction of different phases (gas, solid, liquid) that are in contact with each other. A final capillary force is resulting from a combination of cohesive (for instance surface tension, viscosity, etc. of liquid) and adhesive forces, i.e. affinity of sample molecules to the substrate surface. Here the term "first capillary forces" is to be interpreted as an interaction between the substrate and the sample, i.e. as capillary forces acting between the sample, mainly the liquid part thereof, and the substrate. If the sample at least partially contains molecules that have certain affinity to the substrate, i.e. if adhesive forces are greater than the cohesive forces, then the surface energy of the substrate is greater than the surface energy of the sample together with possible interfacial surface energy of sample-gas. Consequently, the substrate has good wetting properties for the sample. The substrate with good wetting properties for the sample may create a force on the sample so that the sample may travel over the substrate. This force may refer to the first capillary forces. If the substrate does not have good wetting properties for the sample, in order to increase the surface energy of the substrate or to decrease surface energy of the sample and/or interfacial energy of sample-gas addition of solvent may be a solution. The solvent, i.e. a wetting agent such as acetone, ethanol, methanol etc. may be used. The surface energy can be defined by tuning parameters such as: solvent type, solvent-sample ratio, morphology of the substrate, substrate material, etc.

The substrate may be positioned on a surface of any shape which can be rotated around the predetermined axis. Alternatively, the substrate may be a part of the surface itself. Typically, the substrate may be positioned in a sensing chamber. The sensing chamber may have any shape, such as round, rectangular, ellipsoidal, hexagonal, or the like. Typically, the sensing chamber comprises a sample receiving portion and a sensing portion. The sample reception area of the substrate is provided in the sample receiving portion of the sensing chamber and the sensing area of the substrate is provided in the sensing portion of the sensing chamber. The sensing portion may be positioned closer to the predetermined axis of rotation than the sample receiving portion.

A pressure in the sensing chamber may be manipulated. In one embodiment, the sensing chamber may have the atmospheric pressure. Alternatively, the sensing chamber may be isolated from the atmospheric pressure. The pressure in the sensing chamber may relate to the wetting properties of the substrate for the sample, e.g. possible solvent comprised in the sample may evaporate very fast under the atmospheric pressure, hence having a small contribution in wetting properties of the substrate for the sample.

The first capillary forces may be created by narrow passages formed by channels, pillars, etc. comprised in the substrate. During rotation at the first rotational frequency, at least part of the liquid part travels from the sample reception area to the sensing area inside channels comprised in the substrate, which channels create the first capillary forces which act between the liquid part and the substrate. The first capillary forces transport the liquid part against the direction of the first centrifugal force and towards and into the sensing area.

In the present context, the capillary forces may be provided in a number of manners. In a preferred embodiment, the substrate comprises one or more of channels, pillars, paper, a braid, a woven, non-woven and/or knitted element, as elements of this type are known to generate capillary forces. Preferably, this/these elements is/are provided at a surface of the substrate and preferably cover at least a portion of both the sample reception area and the sensing area so that the liquid may travel inside or around these elements from the sample reception area to the sensing area. The tuning of the parameters of such elements, as well as their suitability in a subsequent analysis of the liquid part in the sensing area, is described further below.

The substrate may be provided in a number of manners, including lab-on-a-chip technology.

The removal of the at least a portion of the sample remaining at the sample reception area after the rotating step may be obtained in a number of manners. Preferably, the removal is triggered or even facilitated by the reduction in the rotation itself.

In one situation, an increased gas pressure created in the sensing chamber will cause the at least part of the sample remaining at the sample reception area to travel away from the sensing area and preferably away from the substrate. This increased gas pressure may initially be created by providing the substrate in the sensing chamber, which then preferably has only a single opening, at the sample reception area, and introducing the sample through the opening while not allowing gas to escape the container, thereby increasing the gas pressure therein. The rotation at the first rotational frequency may then be used for preventing sample from leaving the sensing chamber, but allow the sample to do so during the decreasing step. As at least a portion of the sample will be located at the sample reception area where the opening is provided, the pressure relief in the container will be an emission of sample—pushed out of the container by the increased gas pressure.

In another situation, the sample may be sucked away from the sensing chamber, such as by a capillary channel, which is described further below.

In another situation, removing the at least a portion of the sample may be performed by creating a constant flow of the sample further away from the substrate with respect to the predetermined axis. This may be achieved with a capillary directly connected from the loading chamber to the waste chamber The at least part of the sample removed is fed to a waste chamber separate from the sensing chamber. Typically, the waste chamber is positioned further away from the predetermined axis than the sample receiving portion. In that manner, the transport may be facilitated by centrifugal forces. Alternatively, the waste chamber may be the same chamber as the loading chamber.

The at least a portion of the sample remaining at the sample reception area may be transferred through a first conduit connecting the waste chamber to the opening of the sensing chamber.

A suction force may be provided during the removing step so as to transport sample from the sensing chamber to the waste chamber. This may be obtained by having the first conduit be a capillary channel creating a second capillary force facilitating or controlling the removal of the at least part of the sample.

In a preferred embodiment, the first conduit extends from the opening of the sensing chamber to a position closer to the predetermined axis of rotation than the sample receiving portion of the sensing chamber. In this manner, the properties of the first conduit may be adapted to the first and second rotational frequencies, so that the second capillary force exerted by the first conduit acts as a suction force towards the waste chamber or at least away from the sensing chamber. The second capillary force preferably has a component directed toward the predetermined axis of rotation, where the component exceeds the second centrifugal force acting on the sample during rotation at the second rotational frequency but does not exceed the centrifugal force created during the rotating step, i.e. during the rotation at the first rotational frequency.

When the first conduit has a portion extending in a direction having a component toward the axis, the above effect may be achieved. Also, during the applying step and the rotation step, part of the sample may enter the first conduit. However, if the first conduit extends to a position closer to the axis than the sample reception area, the sample will not exit the system through the conduit during the rotating step. It is noted that the sample reception area may be defined as a portion of the substrate or sensing chamber receiving the sample during the applying step, where the amount of sample applied to the system may travel also into the conduit but will, due to the centrifugal forces, reach a certain limit both on the substrate and in the conduit. This limit, on the substrate, may be seen as the limit between the sample reception area and the sensing area.

In fact, a further sample preparation or separation may be performed during the travelling of the part to the sensing area. The part travelling due to capillary forces may itself be separated due to the capillary forces e.g. acting differently on different portions or components of the portion. The higher the affinity of a portion/component, the more of this portion/component will more swiftly attach to the substrate, whereas other portions/components will move further in the direction from the sample reception area to the sensing area. Thus, along this direction, different components/portions of the part may be predominant.

Naturally, the affinity of the substrate may be tailored to a particular type of portion/component. Also, different portions of the substrate may have different affinities to different components in order to enhance the separation of the components over the surface of the substrate and in particular the sensing area.

An additional cause of separation of this part may be physical blocking of larger constituents in the travelling part, if the substrate has channels or openings (such as between elongate rods) which form wider portions toward the sample reception area but more narrow portions toward the sensing area, so that larger constituents will be blocked but liquid and smaller constituents may travel further along the direction.

Having thus separated the part traveling from the sample reception area to the sensing area into portions and deposited such portions (at least predominantly) at different areas of the substrate, different types of measurements may be performed in the different areas of the substrate. Naturally, then the different areas of the substrate may individually be configured to support or cater for the particular measurement to be performed.

For SERS measurements, the material parameters, such as surface material and dimensions, may be selected in accordance with the molecules to be detected.

However, also other types of measurements may be performed, such as fluorescence measurements. It has been found that typical SERS structures, such as structures having elongate elements with conductive tips, may be used for fluorescence measurements especially when e.g. a thin layer (1-20 nm, such as 2-10 nm, such as 3-5 nm) of a dielectric (for example SiO2) is deposited on the tips. In that situation, the SERS signal may be attenuated but the fluorescence much less quenched.

Having then different areas of the substrate where different concentrations of different components of the travelling part are seen, different types of measurements may be performed in order to derive information from the part.

In one situation, the concentrations of one component may be determined over the areas or at a number of positions of the areas and along the direction from the sample reception area toward the sensing area. This may result in a concentration profile along the direction. From this profile, e.g. a concentration of the component in the sample may be determined. Naturally, a concentration only at one position or in one area may alternatively be used.

Naturally, an averaging may be performed along a direction perpendicular to the direction if desired.

Information may also be determined from the concentrations of different components in different areas or from the concentration profiles of different components.

A second aspect of the invention relates to a sample holder comprising a substrate positioned in a sensing chamber,
the substrate comprising a sample reception area and a sensing area, the sensing chamber having a sample receiving portion and a sensing portion, where the sample reception area is provided in the sample receiving portion and the sensing area is provided in the sensing portion, the substrate comprising a portion configured to transfer a liquid part of a sample from the sample reception area to the sensing area by first capillary forces;
a first conduit connected to an opening in the sample receiving portion, wherein the sensing portion is positioned closer to a predetermined axis than the sample receiving portion, and wherein the first conduit extends from the opening to a position closer to the predetermined axis than the sample receiving portion.

In the present context, the sample holder has a sensing chamber wherein a substrate is provided. The sample holder may be shaped in any manner, preferably a disc, and may have one or more sensing chambers/substrates or the like. The sample holder may be configured to be provided in a measuring set-up where a measurement is performed on the sensing area of the prepared substrate.

The substrate has a sample reception area and a sensing area, the sensing chamber having a sample receiving portion and a sensing portion, where the sample reception area is provided in the sample receiving portion and the sensing area is provided in the sensing portion, the substrate comprising a portion configured to transfer liquid part from the sample reception area to the sensing area by first capillary forces.

As is also seen further above, the sensing portion is positioned closer to a predetermined axis than the sample receiving portion, so that the sample holder may be used in the rotational method of the first aspect of the invention. Rotation will force the sample toward the sample receiving portion, while the portion of the substrate may facilitate liquid transport against the centrifugal force.

The portion is configured to transfer liquid by capillary forces. The substrate may comprise multiple elements, the portion being one, and another element being configured to receive the transported liquid and e.g. prepare the other portion for e.g. an analysis.

Preferably, the portion is provided in or at a surface of the substrate.

As mentioned above, the portion preferably comprises one or more channels, pillars, paper, a braid, a woven, non-woven and/or knitted element for generating the capillary forces.

Preferably, as is described below, the portion is furthermore configured to allow an analysis of the liquid or a part thereof, after the rotating step.

The first conduit may be configured to assist for applying a sample to the substrate and removing it.

When the conduit extends from the opening to a position closer to the predetermined axis than the sample receiving portion, the sample extending inside the sensing chamber and to the sample receiving portion but not to the sensing area, during e.g. rotation around the axis, will also extend into the conduit to a position along its length—but usually not to a position much closer to the axis than the sensing area. Then, the sample will not be allowed to escape the system during rotation.

In a preferred embodiment, the substrate comprises a base with pillars extending therefrom, the pillars being spatially displaced from each other. The pillars may have a first end attached to the base and a second end. The pillars may be parallel to each other or may be bendable and be able to lean to each other. The pillars may be made of silicon and/or fused silica and may have an electrically conducting surface on the second end. In one situation, a pillar, or preferably more than 10, 20, 30, 40, 50, 60, 70, 80, 90 or 95% of the pillars, preferably has/have a height being at least 2 times a mean spacing between the pillars. Preferably, the pillars may have a height, i.e. the distance between the base and the second end, of 20-1000 nm, such as 30-500 nm, such as 50-400 nm, such as 75-300 nm. One, more or all pillars may have a height of at least 30 nm, such as at least 40 nm, preferably at least 50 nm, such as at least 100 nm, preferably at least 200 nm, such as at least 400, 500, 600, 700, 1000, 1200, 1400 or 1600 nm. The substrate of this kind may be configured for Surface Enhanced Raman Scattering (SERS) applications. The second end may comprise a tip made of metal such as gold, silver, aluminium, copper, platinum, or a semiconductor material, such as one from a group of III V semiconductors. The tip is a surface at least substantially covering a part of the pillar, which part is the farthest from the base along the pillar. The tip needs not to cover any part of the pillar between the second end and the base.

Such pillars may be used for not only creating the capillary effect but also for enhancing Raman Scattering to facilitate a SERS type measurement on the liquid part or a component thereof.

Thus, firstly, the material of the pillars as well as the spacing there between may be tailored to the liquid part of the sample so as to ensure a sufficient capillary force. These parameters may be selected so that the first capillary forces have a size exceeding a first centrifugal force. Above, an example is given where the first and second centrifugal forces are centrifugal forces at a first and a second rotational frequency.

The sensing chamber may have an opening at the end which is the farthest from the predetermined axis. Preferably, this is the only opening of the sensing chamber. This implies that, preferably, there are no vents connected to the sensing chamber. In one embodiment of the invention, the opening of the sensing chamber is in the sample receiving portion. When the sample is applied to the substrate, i.e. into the sensing chamber, a gas pressure inside the sensing chamber will be increased as the gas is prevented from escaping the sensing chamber. At a later point in time, this increased gas pressure may be used for forcing the at least portion of the sample out of the sensing chamber. This may be when sample is allowed to leave the sensing chamber. Above, examples are described where a first centrifugal force may be used for preventing sample from leaving the sensing chamber and where a lower, the second, centrifugal force allows it.

Due to the extent of the first conduit, the second capillary forces will have a component directed toward the predetermined axis. This component will therefore cause the at least part of the sample remaining at the sample reception area to travel away from the sensing chamber, such as toward a waste chamber.

With this structure and capabilities, the sample holder is configured for the above method where sample is prevented from leaving the sensing chamber during a first rotation but allowed to do so, due to the second capillary forces, at a second, lower rotational frequency.

The first conduit may have a "U" shape or an "s" shape having a first portion and a bend. The first portion may be connected to the opening and the bend may be connected to the first portion and a waste chamber. When the first portion is positioned further away from the predetermined axis than the sensing portion of the sensing chamber and the bend is closer to the predetermined axis than the sample receiving portion, the sample holder is configured to have the operation that, at the above first rotational frequency, no sample is allowed to leave the sensing chamber, but at the second rotational frequency, sample is withdrawn from the sensing chamber through the first portion and the second to arrive in the waste chamber.

The sample holder may further comprise a sample reservoir positioned closer to the predetermined axis than the sample receiving portion and connected to the sensing chamber or the first conduit by the second conduit. The sample reservoir may have any shape, such as round, rectangular, ellipsoidal, hexagonal, or the like. The sample preferably reaches the sample reservoir before it reaches the sensing chamber. The sample reservoir may be configured to receive a volume of sample corresponding to a volume of a sample receiving portion and a combined volume of portions of the conduit and the second conduit positioned closer to the predetermined axis than the sensing portion. The sample reservoir may be connected to one or more vents. In this manner, the sample reservoir may be dimensioned to receive a quantity of sample ensuring that the amount of sample, when applied to the sensing chamber and the substrate, does not extend into the sensing area.

Yet another aspect of the invention relates to an assembly comprising one or more sample holders according to the second aspect of the invention and a rotating device configured to rotate the sample holder around the predetermined axis.

Naturally, the rotating device may be any type of device configured to rotate an element, such as a rotating disc, a record player, or the like. The rotating device preferably has a base and a motor rotating the sample holder in relation to the base.

In one embodiment, the rotating device is configured to rotate the sample holder at each of the first and second rotational frequency. At the first rotational frequency, the first centrifugal force typically exceeds the component of the second capillary forces directed towards the predetermined axis created in the first conduit. At the second rotational frequency, the component exceeds the second centrifugal force acting on the sample in the first conduit. In this manner, the above operation may be obtained. The first and second rotational frequencies may be adapted to the parameters of the substrate and the liquid part, together defining the first capillary forces.

In addition to the centrifugal force acting on the sample due to the rotation, additional forces may be created by applying a pressure difference over the sample, and the transferring of the liquid part towards the sensing area may be controlled by controlling e.g. the surface energy and parameters of the liquid.

The assembly may further comprise a loading chamber. The loading chamber may serve as a chamber that first accepts the sample. In the assembly, the sample may further reach the sample reservoir and finally the sensing chamber. The waste chamber may serve to accept the at least a portion of the sample remaining at the sample reception area of the substrate. Typically, all the chambers may be connected via conduits, capillaries or the like.

The assembly may have a disk shape. The predetermined axis of rotation is then typically perpendicular to the disk and passes through its centre. The centrifugal force generated through the rotation may be controlled and adjusted by controlling the rotation of the disk so that the efficiency of the physical separation of the liquid part from the sample part having the second density is maximized.

The disk may have different diameters, having a diameter or any size. Considering current standard fabrication techniques diameter may be in the range from 1 to 30 cm, preferably 12 cm. The disk may comprise at least one unit. Each unit may comprise at least one substrate. Apart from the substrate, the unit may comprise various systems and devices for handling the sample. In one embodiment, each unit may comprise the loading chamber, sample reservoir, sensing chamber and waste chamber.

As mentioned above, the substrate may be provided with areas having different properties, such as different affinity to different portions of the travelling part and/or different physical structure to perform a physical filtering and/or different characteristic catering for different types of measurements. This caters for the situation where different measurements are performed on different areas of the substrate.

BRIEF DESCRIPTION OF THE DRAWINGS

The invention will now be described in further details with reference to the accompanying drawings, in which.

Figure 1:
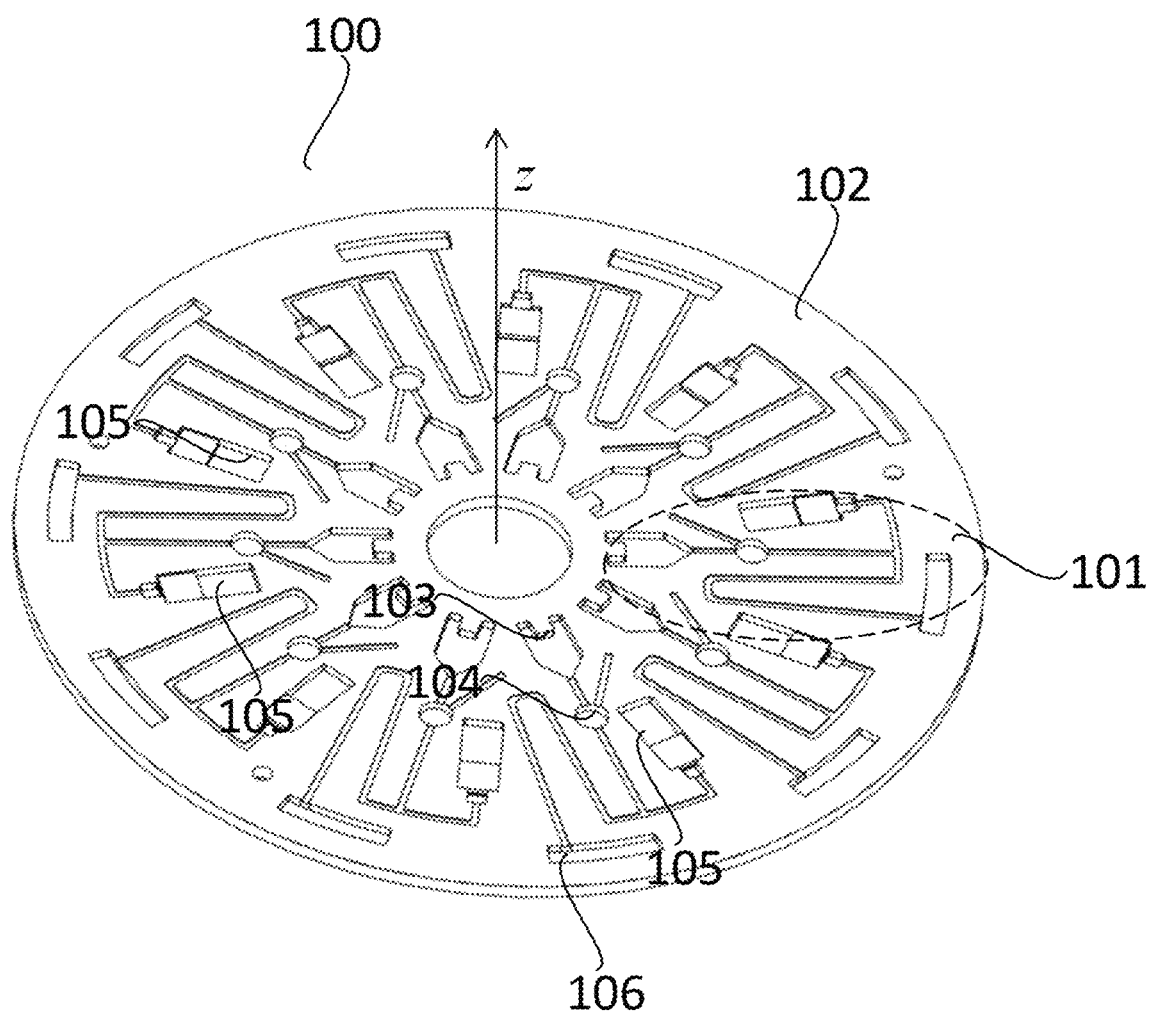
FIG. 1 illustrates an assembly for the substrate preparation.

While the invention is susceptible to various modifications and alternative forms, specific embodiments have been shown by way of example in the drawings and will be described in detail herein. It should be understood, however, that the following description relates to examples of embodiments, and the invention is not intended to be limited to the particular forms disclosed. Rather, the invention covers all modifications, equivalents, and alternatives falling within the spirit and scope of the invention as defined by the appended claims. Furthermore, all the drawings are not to scale, and therefore any ratio extracted from the drawings is not relevant.

DETAILED DISCLOSURE OF THE INVENTION

In its most general aspect, the invention relates to a method for preparing a substrate by separating samples comprising a liquid part having a first density and a sample part having a second density being higher then the first density. Separation is performed mainly by combination of centrifugal and capillary forces.

FIG. 1 illustrates an assembly 100 with 10 units 101 for the substrate preparation and a rotating device 102. Each unit 101 comprises 4 chambers: a loading chamber 103, a sample reservoir 104, a sensing chamber 105 which comprises a substrate, and a waste chamber 106. An axis z indicates the predetermined axis of the rotation of the assembly. The predetermined axis z is passing through a centre of the assembly. The rotating device 102 is configured to rotate the substrate around the predetermined axis z, and therefore the unit 101, with different rotational frequencies. The chambers are positioned such that the loading chamber 103 is the closest to the predetermined axis z. The loading chamber 103 is followed by the sample reservoir 104 placed further towards the outer part of the rotating device. The waste chamber 106 is positioned in the most outer part of the rotating device.

Figure 2:
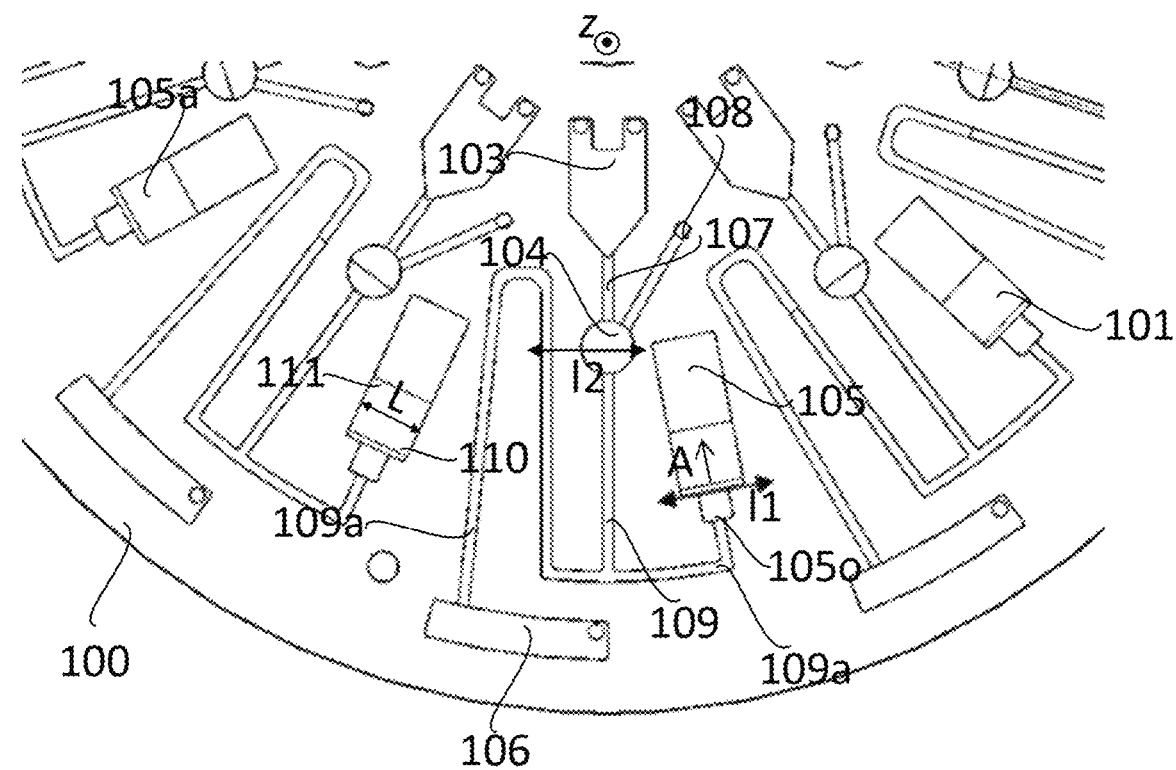
FIG. 2 illustrates a detailed view of the assembly from FIG. 1.

FIG. 2 illustrates a part of the assembly 100 shown in FIG. 1. Three entire units 101 are shown in FIG. 2. A substrate 105a is placed in the sensing chamber 105. The sensing chamber 105 is closer to the centre of the rotating device compared to the waste chamber 106. At first, a sample is loaded into a unit 101 through the loading chamber 103. By rotation of the assembly 100 with a starting rotational frequency around the predetermined axis z, i.e. by a starting centrifugal force created, the sample is transported towards the sensing chamber 105. Namely, from the loading chamber 103, the sample starts to travel through a capillary 107 which connects the loading chamber 103 and the sample reservoir 104. Preferably, the sample reservoir 104 is connected to a vent 108, which is in contact with atmospheric pressure so that no gas resistance is caused by the gas which can be compressed by the sample when filling-up the sample reservoir if there is no vent. Therefore, the sample can freely move and fill-up the sample reservoir 104. The starting rotational frequency which can cause the sample transfer depends on the number of parameters, such as the diameter of the capillary 107, the viscosity and density of the sample, etc. A typical value of this starting frequency could be 30 Hz. With a sample accumulation in reservoir 104 at a certain point, the starting centrifugal force overcomes the capillary force in the capillary 107, and the sample will start to travel towards and through a second conduit, i.e. bottom capillary 109 which extends away from the predetermined axis z. A part of the sample will reach the sensing chamber 105 without touching the substrate 101. The sensing chamber 105 has an opening 105o at the end farthest from the predetermined axis z. This opening 105o is the only opening of the sensing chamber. The sensing chamber does not comprise any vents which would control the gas pressure inside. The opening of the sensing chamber is connected to a first conduit 109a. Preferably, the first conduit 109a has an "s" shape having a first and second bend. The first bend is connected to the opening of the sensing chamber 105o, and the second bend is connected to the first bend and a waste chamber 106. The first bend is positioned further away from the predetermined axes z than the sensing chamber and the second bend is closer to the predetermined axis z than the end of the sensing chamber (which is closer to the predetermined axis z). The second bend of the first conduit 109a is connected to the waste chamber 106. The second conduit 109 and the first conduit 109a are connected at the first band of the first conduit 109a. The first conduit 109a is preferably also a capillary. An alternative structure would have a first portion of the conduit extending directly from the sensing chamber opening to the "second" bend.

As the sample starts to travel towards the sensing chamber 105, gas gets trapped in sensing chamber, as no vents are connected to that chamber 105. This creates a pressure in the sensing chamber 105 which further creates a difference in the level of the sample in the first conduit, i.e. capillary 109a as indicated by 11 and 12, and an opportunity for a precise control of the sample.

Some of the sample may enter the sensing chamber 105 up to a certain limit, as indicated by level L. This limit may be defined by the rotation frequency of the disk. Due to the rotation, and the starting centrifugal force generated, the sample will not by itself travel closer to the rotational axis.

By increasing the starting rotational frequency to the first rotational frequency, the sample boundary in the sensing chamber 105 can be changed. In one situation, the starting frequency may be increased up to 50 Hz. By the frequency increase the sample will enter the sensing chamber 105 up to a certain limit, as indicated with a level L. This limit will be defined by the first frequency of the rotation.

The substrate is of a type such that it creates first capillary forces acting on the liquid part of the sample. The first capillary forces may transport the liquid part against the direction of a first centrifugal force created by rotation at the first rotational frequency and towards the predetermined axis z of the assembly 100. The substrate comprises a sample reception area 110 and a sensing area 111, the sensing area being closer to the predetermined axis z than the sample reception area.

The imbibition of the sample may therefore, be accomplished by the first capillary forces caused by the substrate. The direction of the diffusion is indicated by the arrow A. By keeping the first frequency at the same value, it can be observed that a diffused liquid part of the sample travels by time in the direction of the arrow A. Namely, the first centrifugal force is overpowered by the capillary forces created by the substrate. The first centrifugal force may be adapted with respect to the substrate, i.e. the first capillary forces created by the substrate, and the type of the sample, i.e. its properties such as viscosity, wetting, density, etc. By adjusting the first rotational frequency, the sensing area will be wetted, while it is ensured that negligible amount of the sample part having a second density pollutes the sensing area.

Once the liquid part of the sample reaches the sensing area, i.e. when the sensing area is wetted, at least a portion of the sample remaining at the sample reception area 110 can be removed by tuning the first rotational frequency to a lower value, such as lower than the starting frequency.

Typically, the frequency is decreased to a second rotational frequency which may be only 5 Hz. In that case the gas pressure in the sensing chamber 105 together with the second capillary force created by the first conduit 109a will overcome the first capillary forces and it will push the at least a portion of the sample remaining at the sample reception area through the capillary 109a and towards the reservoir 104 and the waste chamber 106 and thus away from the sensing area.

Figure 3:
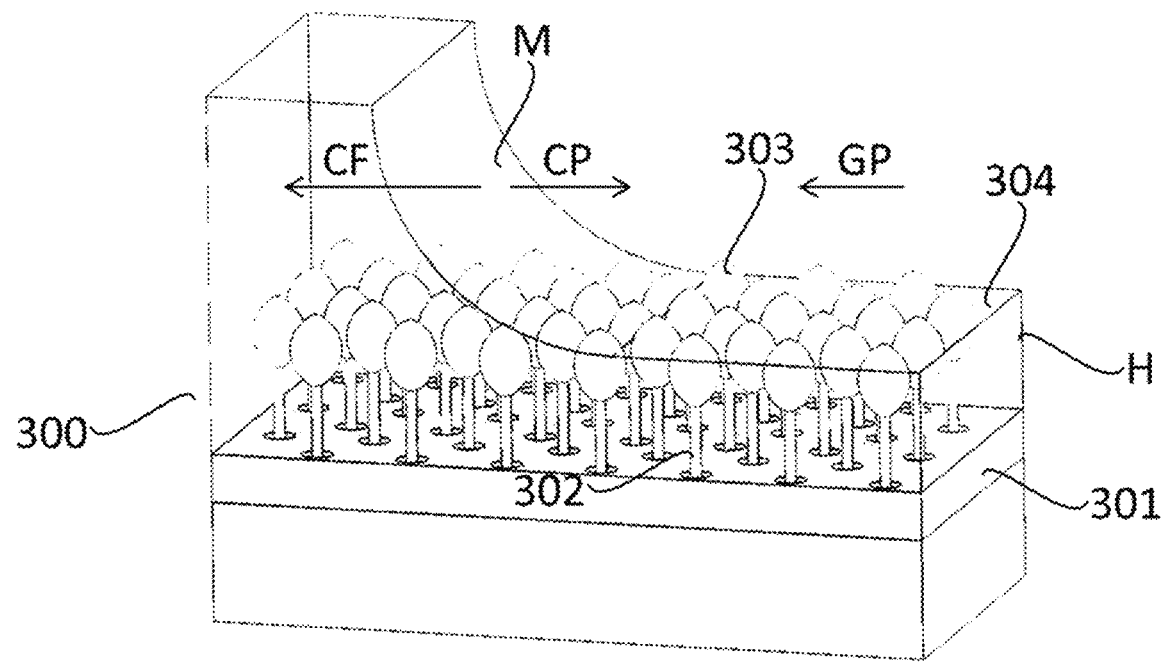
FIG. 3 illustrates a SERS substrate with a typical sample profile.

FIG. 3 illustrates a cross-section of the liquid part of the sample on a SERS substrate 300 with a typical sample profile formed during rotation and delimited by the sample chamber. The SERS substrate 300 comprises a base 301 and a plurality of upright standing pillars 302 with tips 303 with a surface of a SERS active material. The upright standing pillars 302 may be made of fused silica while the tips 303 are typically made of a metal, such as gold, silver, aluminium, copper or platinum, or a semiconductor material, such as one from a group of III-V semiconductors.

As mentioned above, the diffusion of the sample is accomplished by the first capillary forces, as indicated by the arrow CP. The liquid of the sample tends to move along the substrate between the pillars 302 and active tips 303. Furthermore, the first centrifugal force indicated by the arrow CF, as well as the gas pressure GP created by the volume of sample entering the otherwise closed sensing chamber, and which both act in the direction opposite to the first capillary forces. The first centrifugal force and gas pressure will force the at least part of the sample remaining towards the outer end of the rotating device, i.e. away from the predetermined axis of rotation z, but the capillary forces will transport liquid, i.e. lower density portion of the sample, in the opposite direction. Part of the sample with the second density will not be transported to the sensing area it will be physically restrained by the substrate structure. Namely, the first capillary forces created by the substrate refer to existence of narrow passages inside the substrate.

The first centrifugal force CF together with the gas pressure GP and the first capillary forces CF has an influence in the formation of the sample boundaries, the height H of the liquid part thin film and a sample meniscus shape M. Parameters such as diffused thin film shape, its height, the speed of diffusion and the meniscus shape are dependent on equilibrium state of pressure, capillary and centrifugal forces. The thin film 304 formed as a consequence of diffusion, selectively blocks big molecular complexes, i.e. it makes it harder for the big molecular complexes, i.e. sample part with the second density, to travel along the substrate. In the case of the SERS substrate, the morphology of the surface prevents the big molecular complexes to overcome a "forest" of the pillars 302 to diffuse through.

Figure 4:
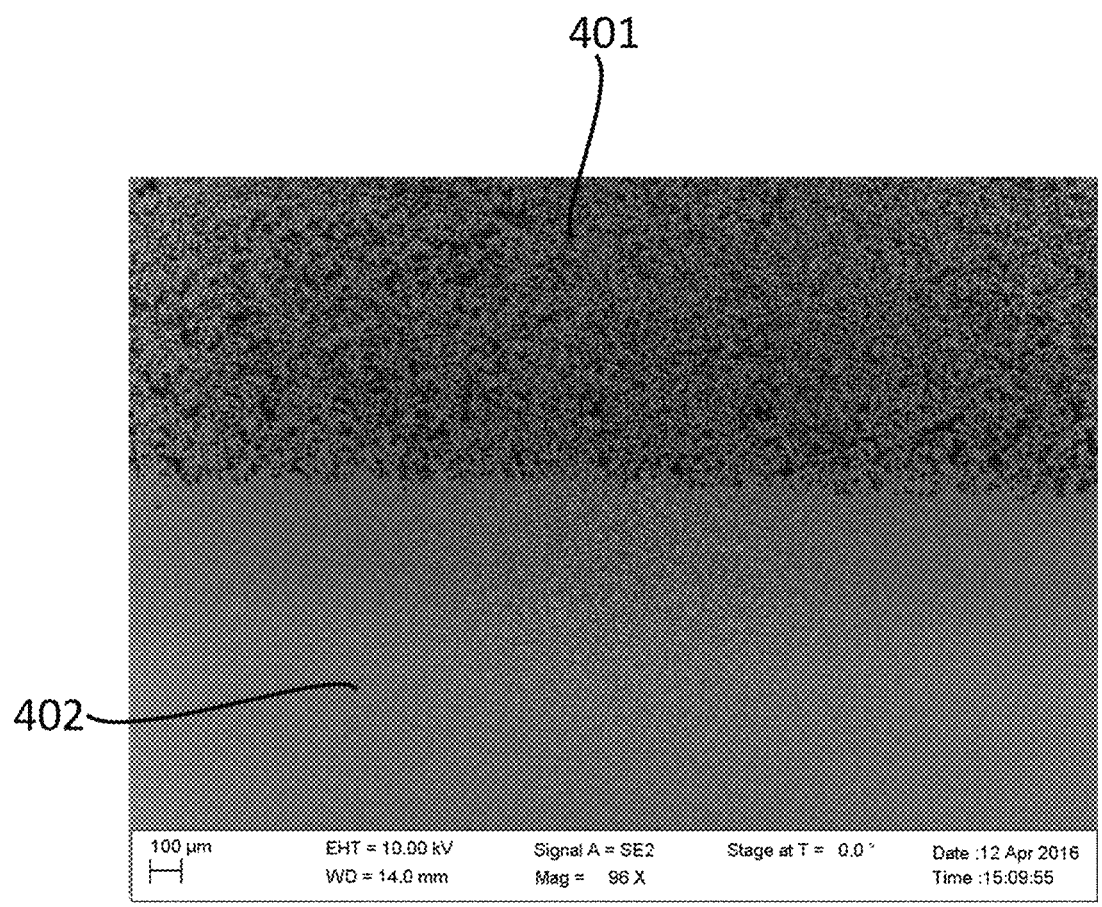
FIG. 4 illustrates an SEM image of a SERS substrate.

FIG. 4 illustrates an SEM image of a SERS substrate after being rotated while being on the rotating device. Two different areas can be clearly identified—an immersed area 401 with a large number of big molecular complexes, and an imbibition area 402, with only a liquid part of the sample.

Figure 5:
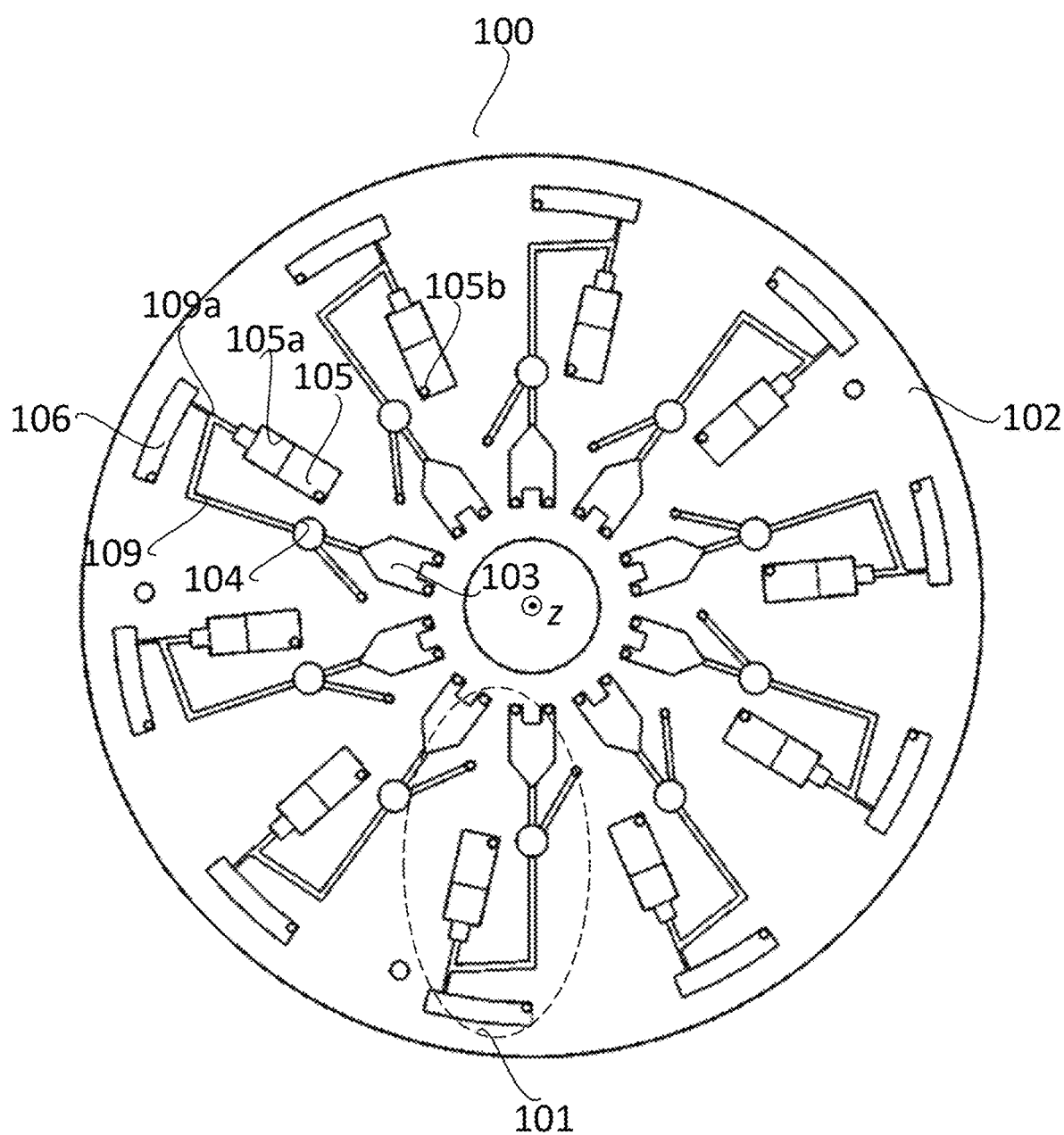
FIG. 5 illustrates an alternative assembly for the substrate preparation.

FIG. 5 illustrates an alternative assembly 100 with 10 units 101 for the substrate preparation and a rotating device 102. Each unit 101 comprises 4 chambers: a loading chamber 103, a sample reservoir 104, a sensing chamber 105 which comprises a substrate and a waste chamber 106. This alternative embodiment may enable removing the at least a portion of the sample by creating a constant flow of the sample further away from the substrate with respect to the predetermined axis. This may be achieved with a capillary 109 directly connected from the loading chamber 103 to the waste chamber 106.

While the assembly 100 is in a stationary position, the sample may be injected through the loading chamber 103. The rotation of the assembly 100 around a predetermined axis z may be established with the first rotational frequency. The sample may start moving from the loading chamber 103, due to the centrifugal force created, to the sample reservoir 104 and fills the capillary 109. A flow rate of the sample depends on the capillary size. The flow rate of the liquid part in the capillary 109 may be different from a flow rate in the capillary 109a. If the flow rate in the capillary 109 is larger than the flow rate in the capillary 109a, a level of the liquid part may start to rise towards the sensing chamber 105 until it reaches equilibrium condition. In this manner the level of the liquid part may be controlled by varying the first rotational frequency. The first rotational frequency may be tuned so that the sample immerses the substrate partially. For instance, the first rotational frequency may be decreased so that the level of the liquid part on the substrate, positioned in the sensing chamber, is held constant. Optionally, there may be a vent 105b in the sensing chamber. Furthermore, as there is the sample flow towards the waste chamber 106 through the capillary 109a, the sample may gradually be transferred to the waste chamber 106 during the rotation.

Figure 6:
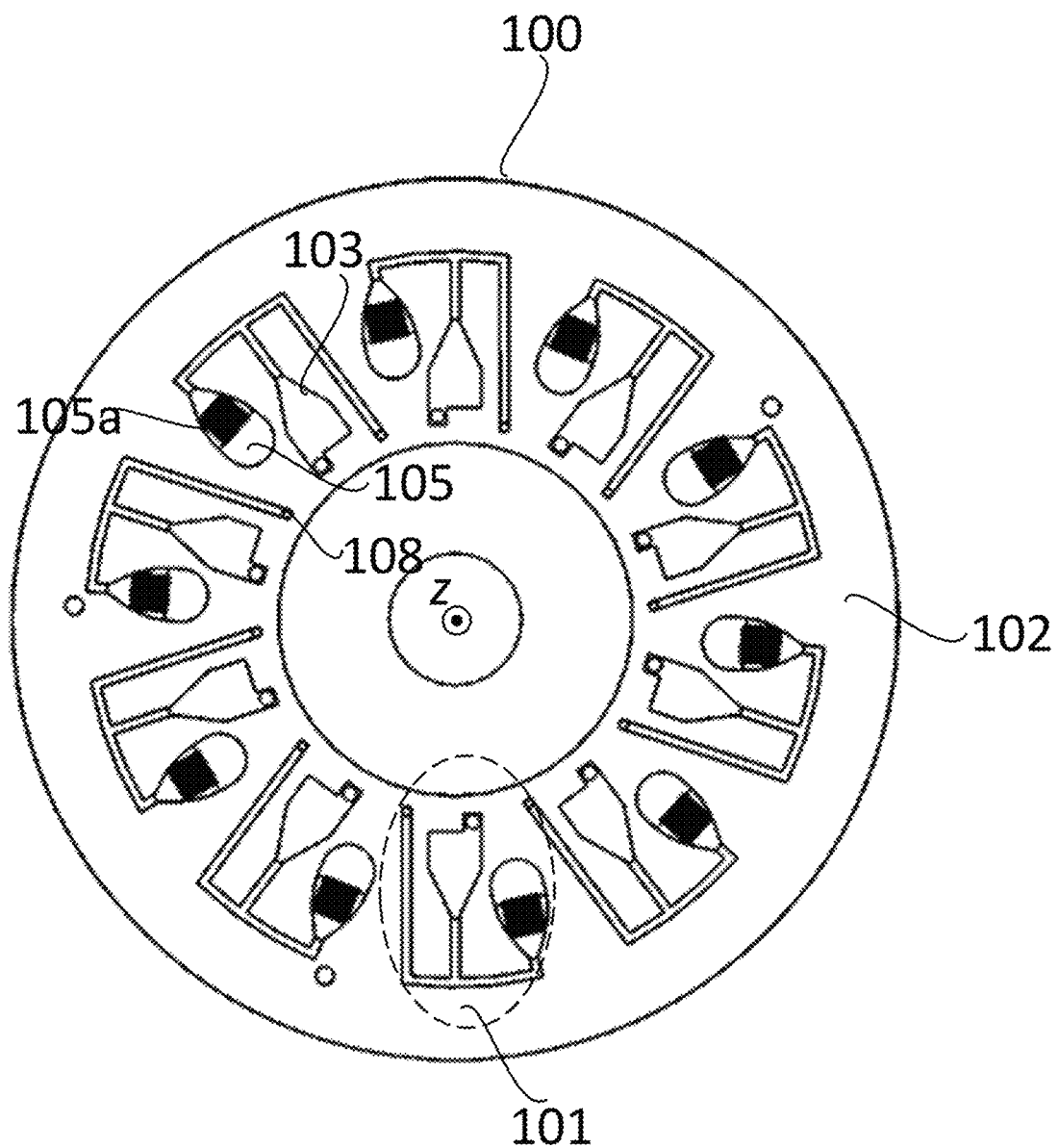
FIG. 6 illustrates yet another alternative assembly for the substrate preparation.

FIG. 6 illustrates yet another alternative assembly 100 with 10 units 101 for the substrate preparation and a rotating device 102. Each unit 101 comprises 2 chambers: a loading chamber 103 and a sensing chamber 105 which comprises a substrate. A substrate 105a is placed in the sensing chamber 105. At first, a sample is loaded into a unit 101 through the loading chamber 103 while the assembly is in stationary position. A vent 108 is implemented for ventilation during the sample loading. The rotation of the assembly around the predetermined axis z is established with the first rotational frequency. In this stage the sample does not reach the substrate 105a. The sample will reach the substrate 105a by tuning the rotational frequency so that it compensates pressure in the sensing chamber 105. The rotational frequency will be changed to a second rotational frequency typically larger than the first rotational frequency. In this case the second rotational frequency may be tuned so that, in an equilibrium condition, a level of the liquid part of the sample in the sensing chamber 103 is above the substrate 105a, partially immersing the substrate 105a. Finally, the assembly is brought back to stationary position. As there are no more centrifugal forces acting on liquid part of the sample, pressure in the sensing chamber 105 pushes the liquid part back to the loading chamber 103. In this case the loading chamber 103 has a role of a waste chamber.

Figure 7:
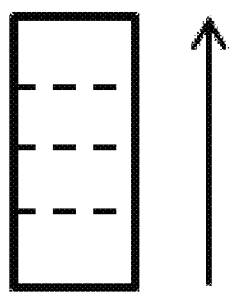
FIG. 7 illustrates a substrate with different areas.

In FIG. 7, a substrate is illustrated having different areas. The use and advantages thereof is described above. The direction of travel of the part of the sample is illustrated. Then, the lower area may hold a solid component of the travelling part if the first (from below) hatched line illustrates a physical filter, such as an interface between areas having larger (below) and narrower channels. The other areas may be areas with different surface characteristics to generate different affinities to different components. Then, different measurements may be made in the different areas.

The invention claimed is:

1. A sample holder, comprising:
    a sensing chamber, the sensing chamber having a sample receiving portion and a sensing portion; and
    a substrate positioned in the sensing chamber, the substrate including a sample reception area and a sensing area the sample reception area in the sample receiving portion of the sensing chamber, the sensing area in the sensing portion of the sensing chamber, the substrate including a portion configured to transfer a liquid part of a sample from the sample reception area to the sensing area by first capillary forces, wherein the sensing chamber has an end and a single opening, the single opening in the end, wherein the sample holder further includes a first conduit connected to the single opening in the sample receiving portion, wherein the sensing portion is positioned closer to a predetermined axis than the sample receiving portion, wherein the end is a farthest end from the predetermined axis, and wherein the first conduit extends from the single opening to a position closer to the predetermined axis than the sample receiving portion.

2. The sample holder according to claim 1, wherein the substrate comprises a base with pillars extending therefrom, the pillars being spatially displaced from each other, the pillars having a first end attached to the base and a second end.

3. The sample holder according to claim 1, the first conduit having a first portion and a bend, the first portion being connected to the opening, the bend being connected to the first portion and a waste chamber, the first portion being positioned further away from the predetermined axis than the sensing portion and the bend being closer to the predetermined axis than the sample receiving portion.

4. The sample holder according to claim 1, further comprising a sample reservoir positioned closer to the predetermined axis than the sample receiving portion and connected to the sensing chamber or the first conduit by a second conduit, the sample reservoir being configured to receive a volume of sample corresponding to a volume of the sample receiving portion and a combined volume of portions of the first conduit and the second conduit positioned closer to the predetermined axis than the sensing portion.

5. An assembly comprising one or more sample holders according to claim 4 and a rotating device configured to rotate the one or more sample holders around the predetermined axis.

6. The assembly according to claim 5, wherein the rotating device is configured to rotate the one or more sample holders at each of a first rotational frequency and a second rotational frequency, where at the first rotational frequency, a first centrifugal force exceeds a component of a second capillary forces directed towards the predetermined axis created in the first conduit, at the second rotational frequency, a second centrifugal force acts on the sample in the first conduit, the component exceeding the second centrifugal force.

* * * * *